US007238843B2

(12) United States Patent
Pohl

(10) Patent No.: US 7,238,843 B2
(45) Date of Patent: *Jul. 3, 2007

(54) PROCESS FOR THE PRODUCTION OF ALKYLAROMATICS

(75) Inventor: Stephen L. Pohl, Wayne, NJ (US)

(73) Assignee: ABB Lummus Global, Inc., Bloomfield, NJ (US)

( * ) Notice: Subject to any disclaimer, the term of this patent is extended or adjusted under 35 U.S.C. 154(b) by 518 days.

This patent is subject to a terminal disclaimer.

(21) Appl. No.: 10/376,683

(22) Filed: Feb. 28, 2003

(65) Prior Publication Data

US 2004/0171899 A1    Sep. 2, 2004

(51) Int. Cl.
   *C07C 2/68*    (2006.01)
(52) U.S. Cl. ..................... 585/467; 585/448
(58) Field of Classification Search ............ 585/448, 585/467
   See application file for complete search history.

(56) References Cited

U.S. PATENT DOCUMENTS

| 2,909,574 | A | * | 10/1959 | Woodle ............... 585/448 |
| 3,200,164 | A |   | 8/1965 | Gerald |
| 3,205,277 | A |   | 9/1965 | Pollitzer et al. |
| 3,428,701 | A |   | 2/1969 | Ward |
| 3,843,739 | A |   | 10/1974 | Harper et al. |
| 4,008,290 | A |   | 2/1977 | Ward |
| 4,048,243 | A |   | 9/1977 | Ruckelshauss |
| 4,051,191 | A |   | 9/1977 | Ward |
| 4,083,886 | A |   | 4/1978 | Michalko |
| 4,107,224 | A |   | 8/1978 | Dwyer |
| 4,169,111 | A |   | 9/1979 | Wight |
| 4,215,011 | A |   | 7/1980 | Smith, Jr. |
| 4,232,177 | A |   | 11/1980 | Smith, Jr. |
| 4,242,530 | A |   | 12/1980 | Smith, Jr. |
| 4,250,052 | A |   | 2/1981 | Smith, Jr. |
| 4,302,356 | A |   | 11/1981 | Smith, Jr. |
| 4,307,254 | A |   | 12/1981 | Smith, Jr. |
| 4,316,997 | A |   | 2/1982 | Vaughan |
| 4,371,714 | A |   | 2/1983 | Young |
| 4,423,254 | A |   | 12/1983 | Olah |
| 4,443,559 | A |   | 4/1984 | Smith, Jr. |
| 4,459,426 | A |   | 7/1984 | Inwood et al. |
| 4,469,908 | A |   | 9/1984 | Burress |
| 4,540,831 | A |   | 9/1985 | Briggs |

(Continued)

FOREIGN PATENT DOCUMENTS

EP    0 733 608 B1    1/2000

OTHER PUBLICATIONS

PCT International Search Report dated Sep. 15, 2004, for PCT/US2004/005548, filed Feb. 25, 2004.

*Primary Examiner*—Thuan Dinh Dang
(74) *Attorney, Agent, or Firm*—Dilworth & Barrese, LLP

(57) ABSTRACT

A process for producing an alkylaromatic compound includes contacting a dilute olefin feed with a lean oil stream containing aromatic compound and alkylaromatic compound in an absorption zone to provide an alkylation reaction stream containing aromatic compound, alkylaromatic compound and olefin. The alkylation reaction stream is reacted under alkylation reaction conditions in an alkylation reaction zone to provide an effluent containing the aromatic compound and alkylaromatic compound. The effluent of step is separated into the lean oil stream which is recycled to the absorption zone and a product portion from which an alkylaromatic product is recovered.

31 Claims, 1 Drawing Sheet

U.S. PATENT DOCUMENTS

| | | |
|---|---|---|
| 4,570,027 A | 2/1986 | Boucher et al. |
| 4,587,370 A | 5/1986 | DeGraff |
| 4,695,665 A | 9/1987 | De Graff |
| 4,849,569 A | 7/1989 | Smith, Jr. |
| 4,857,666 A | 8/1989 | Barger et al. |
| 4,870,222 A | 9/1989 | Bakas et al. |
| 4,891,458 A | 1/1990 | Innes et al. |
| 4,922,053 A | 5/1990 | Waguespack et al. |
| 5,003,119 A * | 3/1991 | Sardina et al. ............... 585/323 |
| 5,030,786 A | 7/1991 | Shamshoum et al. |
| 5,118,894 A | 6/1992 | Le |
| 5,177,285 A | 1/1993 | Van Opdorp et al. |
| 5,334,795 A | 8/1994 | Chu et al. |
| 5,336,821 A | 8/1994 | DeGraff et al. |
| 5,430,211 A | 7/1995 | Pogue et al. |
| 5,602,290 A | 2/1997 | Fallon |
| 5,723,710 A | 3/1998 | Gajda et al. |
| 5,856,607 A | 1/1999 | Kim |
| 5,902,917 A | 5/1999 | Collins et al. |
| 5,977,423 A | 11/1999 | Netzer |
| 5,998,684 A | 12/1999 | Ho et al. |
| 6,060,632 A | 5/2000 | Takamatsu et al. |
| 6,096,935 A | 8/2000 | Schulz et al. |
| 6,252,126 B1 | 6/2001 | Netzer |

* cited by examiner

PROCESS FOR THE PRODUCTION OF ALKYLAROMATICS

FIELD OF THE INVENTION

The invention generally relates to an alkylation process for the production of an alkylaromatic from an olefin and an aromatic and, more particularly, to the production of ethylbenzene by reacting ethylene and benzene in the presence of a zeolite catalyst.

BACKGROUND OF THE INVENTION

Various processes for the production of alkylbenzene by the alkylation of benzene with an olefin are known in the art. Among the most common olefins used are ethylene and propylene. The alkylation of benzene with ethylene produces ethylbenzene. The alkylation of benzene with propylene produces cumene.

Alkylbenzenes, such as ethylbenzene and cumene (isopropylbenzene) are important industrial chemicals. In particular, ethylbenzene is commonly used to produce styrene, which may be polymerized to produce polystyrene, and cumene may be used as an additive for high-octane fuels or to produce phenol and acetone. Various methods are known for the production of alkylbenzenes, including ethylbenzene, which may be made by the alkylation of benzene with ethylene, as follows:

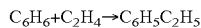

Successive alkylations generally occur, producing diethylbenzenes and other higher ethylated benzenes.

The following reaction is typical:

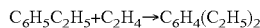

Other coupling reactions occur to a minor extent, yielding materials such as butylbenzenes, diphenylethanes and higher boiling compounds. The mixture may be distilled to recover ethylbenzene, benzene and higher ethylated benzenes, and the higher ethylated benzenes may be transalkylated with benzene to form additional ethylbenzene. Processes related to alkylation reactions are disclosed in U.S. Pat. No. 5,003,119 to Sardina et al., which is incorporated by reference herein.

As an example, alkylation reactions may take place in a single fixed-bed reactor; and may occur adiabatically, i.e., no external heating or cooling is supplied, over a zeolite catalyst at an operating pressure high enough to maintain the reactor contents in the liquid phase. Carrying out the reaction in the liquid phase is more efficient than doing so in the gas phase and requires less catalyst. The reaction may be carried out with multiple catalyst beds in series, e.g., the benzene may be fed to the first catalyst bed and the ethylene may be fed separately to each catalyst bed. This multi-stage injection of ethylene may be used because it provides high local benzene-to-ethylene ratios in the catalyst beds for improved product selectivity, purity and extended catalyst run length. The reactor design parameters may be adjusted to ensure the optimum temperature profile for each catalyst bed, resulting in increased catalyst run times and minimum by-products.

While high purity ethylene is ideal for producing alkylaromatics, it is more expensive to produce than dilute ethylene. Dilute sources of ethylene are readily available, and alkylators may be configured in various ways to optimize alkylaromatic production with ethylene feeds of different concentrations. However, ethylene feeds with ethylene concentrations lower than about 70 mol % generally are not suitable to produce alkylaromatics because non-ethylene components in the feed do not dissolve in alkylators at reasonable pressures, which are typically less than 1500 psig. This results in the alkylator operating in the gas phase, which is less efficient and which consumes far more catalyst than a liquid phase alkylation reaction. Even ethylene feeds containing concentrations of ethylene higher than 70 mol % are not suitable for producing alkylaromatics if they also contain significant amounts of inert low molecular weight impurities (which do not react with the catalyst but which have relatively low boiling points), e.g., hydrogen, methane, ethane, nitrogen, carbon dioxide, carbon monoxide and, less commonly, butane and pentane. Hydrogen, methane, nitrogen, carbon dioxide and/or carbon monoxide, in amounts of about 5 mol % or higher, are especially problematic because the low boiling points of these low molecular weight impurities make them particularly difficult to dissolve in the alkylator.

Thus, there is a need for a process which allows for the efficient alkylation of aromatics, such as benzene, to form alkylaromatics, such as ethylbenzene. Further there is a need for a process which utilizes dilute sources of olefin, such as ethylene, minimizes olefin waste and reduces the amount of catalyst consumed during the alkylation reaction.

SUMMARY OF THE INVENTION

A process for producing an alkylaromatic compound is provided herein. The process comprises (a) contacting a dilute olefin feed with a lean oil stream containing aromatic compound and alkylaromatic compound in an absorption zone to provide an alkylation reaction stream containing aromatic compound, alkylaromatic compound and olefin; (b) reacting the alkylation reaction stream of step (a) under alkylation reaction conditions in an alkylation reaction zone to provide an effluent containing the aromatic compound and alkylaromatic compound; (c) separating the effluent of step (b) into the lean oil stream which is recycled to the absorption zone of step (a) and a product portion; and, (d) recovering an alkylaromatic product from the product portion of step (c).

The invention improves upon known processes by allowing the efficient production of alkylaromatics from the reaction of relatively dilute sources of olefin with an aromatic.

DETAILED DESCRIPTION OF THE PREFERRED EMBODIMENT(S)

Figure 1:
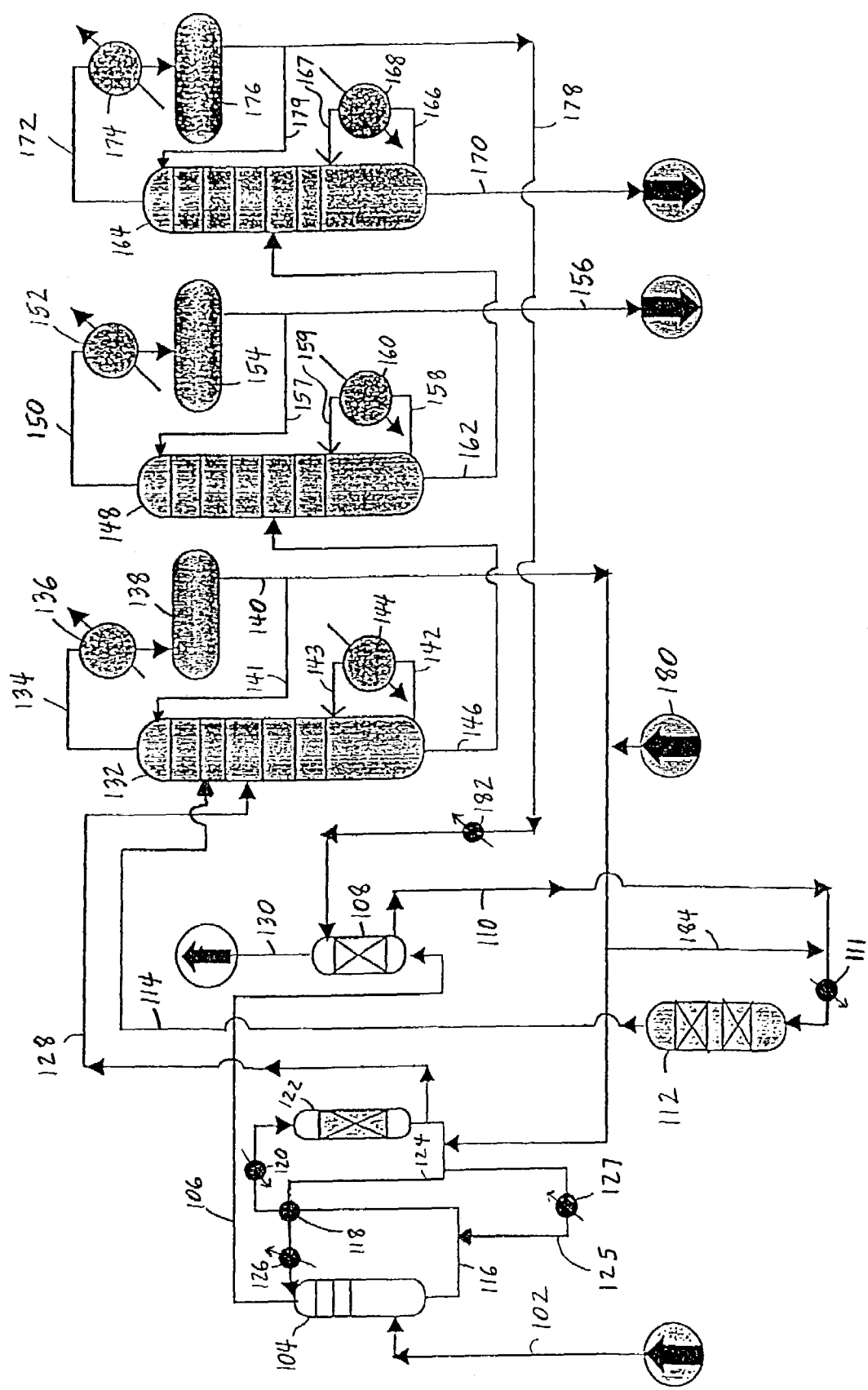
FIG. 1 is a schematic flow chart of a preferred process for producing an alkylaromatic.

The invention is suitable for use with an extremely wide range of ethylene feed concentrations, ranging from feeds with ethylene concentrations of about 95 mol % or more to feeds with ethylene concentrations as low as about 3 mol %. The invention is also suitable for use with ethylene feeds which include significant amounts of low molecular weight impurities. Thus, the invention may be particularly advantageous in circumstances where the ethylene feed contains about 70 mol % or less ethylene, or low molecular weight impurities in amounts of about 5 mol % or higher, or both, i.e., a feed that is generally not suitable for known alkylation processes.

In a preferred process of the invention, an alkylaromatic, such as ethylbenzene, may be produced as follows: Ethylene vapor feed (e.g., 3-95 mol %), such as that from steam crackers, cat crackers, FCC (fluid catalytic cracking) units, refineries, cokers, or other sources, is fed to an absorber and contacted with a chemical stream which absorbs most of the ethylene, separates hydrogen and other inert low molecular weight impurities, such as e.g. methane, ethane, nitrogen, carbon dioxide and carbon monoxide, and less commonly butane and pentane, for diversion to a vent scrubber, and then transports the absorbed ethylene to an alkylator where it is reacted with benzene.

Referring to FIG. 1, ethylene feedstock is fed, via line 102, to a vent absorber 104. In the absorber 104 most of the ethylene is absorbed into a "lean" oil stream (i.e., a stream containing substantially no ethylene) comprising benzene and ethylbenzene.

The absorber may be a tray or packed absorber or combined packed column-tray absorber, and may be operated at a preferred temperature of about 6° C. to about 100° C., more preferably between about 10° C.-20° C.; and at a preferred pressure of about 0-50 bar, more preferably between about 10-30 bar. The absorber operates in the vapor continuous mode (i.e., gas phase) and may have from 5 to 150 distillation trays. The preferred number of trays is typically 40. Distillation trays can be valve, sieve, mutiple-downcomer or other types. Mutiple-downcomer trays are preferred in circumstances where the absorber has high liquid loading as in the present example. The liquid loading for the absorber is typically from 10 to 60 gallons per square foot, preferably about 45 gallons per square foot. The absorber can also be designed with either a random or structured packing. A number of distillation stages provided by the packing can range from 4 to 75, preferably 15. The absorber 104 has operating parameters which include a jet flood safety factor which is preferably between 1.1 and 1.75, with a more preferred jet flood safety factor of about 1.35. The absorber 104 has a system factor which is between about 0.5 to about 1.0, preferably about 0.85 for this system. The absorber is constructed using normal carbon steel. The use of alloys such as stainless steels is not required. The absorber trays can be constructed from either carbon or stainless steels. If a packing is used it can be either carbon or stainless steel.

A vapor which may comprise one or more inert low molecular weight impurities and/or other impurities, e.g. hydrogen, nitrogen, methane, ethane, propane, carbon dioxide, carbon monoxide, butane, pentane, hexane, water, non-aromatics, benzene, toluene, ethylbenzene, and one or more polyethylbenzenes (PEBs), such as diethylbenzene, triethylbenzene and the like, is sent, via line 106, to the vent scrubber 108 wherein the aromatics, mostly benzene and PEB, are recovered during contact with a PEB stream and are sent, via line 110, to the transalkylator 112.

The vent scrubber may be a tray or packed vent scrubber, and may be operated at a preferred temperature of about 6° C. to about 125° C., more preferably between about 10° C.-40° C.; and at a preferred pressure of about 0-50 bar, more preferably between about 10-30 bar. The vent scrubber operates in the vapor continuous mode. The vent scrubber may have from 5 to 100 distillation trays. The preferred number of trays is typically 20. The type of distillation trays can be valve, sieve, mutiple-downcomer or other types. The preferred tray type is valve. The liquid loading for the vent scrubber is typically from about 0.1 to about 5 gallons per square foot. The preferred liquid loading is about 0.5 gallons per square foot. The vent scrubber can also be designed with either random packing, e.g., dumped packing such as Pall ring packing or IMTP packing (Koch Engineering Co., Inc., Wichita, Kans.), or structured packing. The number of distillation stages provided by the packing can be from 4 to 75. The preferred number of stages is typically 10. Preferred operating parameters include a jet flood safety factor between about 1.1 and about 1.75, more preferably about 1.25. The system factor can range from about 0.5 to about 1.0 for this system, and is preferably about 1.0. The vent scrubber is constructed using normal carbon steel. The use of alloys such as stainless steels is not required. The vent scrubber trays can be constructed from either carbon or stainless steels. When a packing is used it can be either carbon or stainless steel.

Generally, hydrogen, methane, ethane, water and small amounts of $C_6$ non-aromatics and benzene are vented from the vent scrubber 108 through line 130. The ethylene which is not absorbed into the lean oil stream in the absorber 104, preferably less than 0.1 mol % of that which was sent to the absorber, also exits the absorber via line 106 in the overhead vapor and a very small amount can be recovered in the vent scrubber 108.

The effluent from the absorber 104, "rich" oil containing relatively high levels of ethylene, generally comprises about 60 wt % to about 90 wt %, preferably about 80 wt % benzene; about 5 wt % to about 40 wt %, preferably about 15 wt % ethylbenzene; and about 0.1 wt % to about 5 wt %, preferably at least about 1 wt % ethylene, depending, in part, on the purity of the ethylene source; and generally some diethylbenzene, ethane, methane and hydrogen. The rich oil exits the absorber via line 116, where it is heated against the lean oil stream, in line 124, in the alkylator feed/effluent interchanger 118 and then by the alkylator heater 120 before entering the alkylator reactor 122. The rich oil stream is heated in the interchanger 118 from about a 10° C.-100° C. inlet temperature to about a 100° C.-250° C. outlet temperature by cooling the lean oil stream from about 200° C.-250° C. to about 20° C.-100° C. These temperatures can be varied to optimize the energy balance in ways well known in the art. For example, a large interchanger may be used to transfer large amounts of heat between streams to save energy costs, or the interchanger may be removed entirely to save on equipment costs in circumstances where energy is relatively inexpensive. The alkylator heater 120 operates between about 175° C. to about 250° C.

The alkylator 122 is preferably a fixed bed reactor containing at least one bed of loose catalyst such as zeolite, for example, zeolite BEA (beta), zeolite MWW, zeolite Y, Mordenite catalyst, MFI catalyst, Faujasite catalyst; or any other molecular sieve catalyst suitable for liquid phase alkylation or combinations of any of the above catalysts. Zeolite BEA is preferred. The reactor operates in an adiabatic, liquid filled, single-phase mode. The alkylator may be an up-flow or down-flow reactor. Down-flow is the preferred configuration. It is preferred that the alkylator 122 operates in the temperature range of about 150-300° C., more preferably from about 180-250° C.; and at a pressure of about 150-2,000 psig, more preferably about 300-1000 psig; with a typical liquid hourly space velocity (LHSV) in the range of about 2-1,000, more preferably about 4-100. The aromatic to olefin ratio is typically from about 1.0 to about 10, preferably about 1.5 to about 3.5. The alkylator 122 can operate in the liquid phase because the rich oil contains very little hydrogen or other inert low molecular weight impurities, for example, methane, ethane, carbon dioxide, carbon monoxide, nitrogen or the like, since they were separated in the absorber 104 and sent via the overhead vapor in line 106 to the vent scrubber 108, as described above. Removing these gases at the absorber 104 is significant because it reduces the pressure required in the alkylator 122 for the reaction to be carried out in the liquid phase, and liquid phase alkylation is generally more desirable because it is more efficient and requires relatively less catalyst than a gas phase reaction. It is preferred that the phenyl (i.e., benzene) to ethyl ratio in the alkylator 122 be between about 1.5 to 1 and about 10 to 1, more preferably about 2.75 to 1, which will result in excellent catalyst selectivity, i.e. high yield, and stability. Water can be added to the alkylation operation to improve yield. The water concentration is maintained between 0 ppm to about 1500 ppm, about 500 ppm is preferred. Conversion of ethylene in this reaction is essentially complete.

As discussed above, the alkylator 122 can be operated in either a down-flow or up-flow manner, though the examples discussed herein are for a reactor being operated in a down-flow manner. There is a pressure drop through the alkylator between about 1 psi and about 15 psi, preferably about 5 psi. Preferably about 5 wt % to about 99 wt %, more preferably about 75 wt % to about 95 wt %, of the lean oil stream from the alkylator is directed, via line 124, to the top of the absorber 104, after passing through the alkylator feed/effluent interchanger 118, where it is cooled against absorber bottoms (rich oil), and through the absorber chiller 126 where it is chilled against refrigerant. The lean oil is chilled to between about 6 to about 100° C., preferably about 12° C. In order to control the temperature rise within the alkylator 122 a portion of the lean oil stream in line 124 may optionally be recycled in a known manner by a recycle line 125 which directs some of the lean oil in line 124 to line 116 at any point on line 116 between the absorber 104 and the alkylator 122. The recycle line 125, or line 116, may optionally include a cooler 127 to further control the temperature rise within the alkylator 122. The exact arrangements and adjustments may easily be made by those who practice in the art such that the range of temperature rise can be controlled to less than about 10° C. so that optimum reaction conditions are maintained. A narrow temperature range will optimize the selectivity, minimize byproduct formation and lessen catalyst deactivation. The remaining lean oil stream from the alkylator 122 is sent, via line 128, to a benzene distillation column 132.

Optionally, the alkylator 122 can include multiple beds in spaced, stacked arrangement to form sequential stages of alkylation reaction zones. Multiple olefin feed inlets can be respectively positioned between the stages. For example, high purity polymer grade ethylene (purity of about 100 mol % to about 70 mol %) can optionally be added directly to one or more stages of the multiple bed alkylator (not shown) in amounts which preferably maintain the olefin to aromatic (e.g., benzene) ratio in the alkylator between about 10 to 1 and about 30 to 1, more preferably about 30 to 1, which will result in excellent catalyst selectivity, i.e. high yield, and stability. For example, a six bed alkylator can be used, where dilute ethylene is reacted in the first bed and high purity ethylene is fed to each of the following five beds. At any or all of the beds the stream leaving the alkylator bed may be cooled before additional high purity ethylene is added. The amount of additional ethylene added is about the same as the amount of ethylene that is reacted in the preceding bed. This method will maintain the fluid stream in the alkylator in the liquid phase and prevent vaporization. This results in the efficient use of the catalyst and will minimize overall production costs. In these circumstances it is preferred that the stream in the alkylator be cooled to about 200° C. by generating steam or heating an internal process stream at or before the location where the polymer grade ethylene is added. This additional step will further lower overall production costs.

In another optional arrangement, the lean oil stream in line 124, which may contain significant amounts of ethane and relatively small amounts of ethylene, may be directed to an ethane distillation column (not shown). The result of this optional step would be to recover a lean oil from a bottom of the ethane distillation column, which would be directed to the absorber 104 and, additionally, to recover ethane at a top of the ethane distillation column. This recovered ethane would include relatively small amounts of methane and may be particularly suitable for use in a thermal cracking unit.

Returning to the vent scrubber 108, in a preferred embodiment the aromatics from the vent scrubber 108 are comprised primarily of about 4 parts of benzene to about 1 part of PEB and are directed, via line 110, to the transalkylator 112. Normally line 110 will include a heater 111 at a point between the intersection of lines 110 and line 184 (discussed below) and the transalkylator 112, as shown. The heater 111 operates between about 170° C. to about 260° C., the preferred temperature is about 200° C. In the transalkylator 112 the aromatics are reacted over a catalyst and about a 50% conversion occurs which results in the liquid leaving the transalkylator 112 comprising about 5 parts of benzene to about 1 part of PEB.

Line 114 carries this liquid effluent from the transalkylator 112 to the benzene distillation column 132. The effluent from the transalkylator 112 is normally fed to the benzene distillation column 132 above the lean oil effluent in line 128 from the alkylator, though it may be fed to the benzene distillation column at the same location or below line 128. The location of the two distillation column feeds are optimized to minimize heat input to a benzene distillation column reboiler 144, which is discussed below.

It is preferred that the transalkylator 112 operate in the temperature range of about 170-260° C., more preferably about 200-250° C.; and at a pressure of about 150-2000 psig, more preferably about 300-600 psig; with a typical LHSV in the range of about 1-1,000, more preferably about 2-100. The transalkylation reaction occurs in the liquid phase, adiabatically and essentially thermally neutral, i.e. with a very small temperature rise of less than about 2° C. The transalkylator 112 can be either an up-flow or down-flow reactor, a down-flow reactor is preferred.

FIG. 1 shows three distillation operations which are employed to separate the effluents from the alkylator 122, in line 128, and the transalkylator 112, in line 114, in a known manner. The effluents in lines 128 and 114 are directed to the benzene distillation column 132 where benzene is recovered from the crude ethylbenzene product. The benzene is distilled overhead as a vapor which is sent via line 134 to a condenser 136 where it is liquefied and held in an accumulator 138. The condenser 136 can produce steam or can heat other process streams, and may use cooling water or air. The operating parameters are set to optimize the energy efficiency of the process. The benzene is drawn off via line 140 and added to the lean oil stream in line 124 which is directed to the vent absorber 104. Benzene is returned to the lean oil flow in order to maintain the proper concentration of benzene in line 124, so that there is proper selectivity in the alkylator 122. The alkylation reaction is equilibrium controlled, i.e., the aromatic to olefin ratio determines the monoselectivity. Some of the benzene in line 140 may be diverted, via line 184, to line 110 and on to the transalkylator 112. As with the alkylator 122, maintaining the proper concentration of benzene in the transalkylator 112 improves selectivity. Fresh benzene can also be added in a variety of locations from a benzene source 180. The exact location is not important to the performance of the unit.

Returning to the benzene distillation column 132, line 141 carries a portion of the stream in line 140, i.e. a liquid reflux stream, to the top of the benzene distillation column 132 to maintain the distillation operation. Line 142 carries a liquid stream from the bottom of the benzene distillation column 132 to a reboiler 144. A vapor, and possibly some liquid, is returned back to the benzene distillation column 132 via line 143. This vapor drives the distillation operation in the benzene distillation column 132.

A remaining portion of the benzene distillation column bottom stream, which comprises ethylbenzene, PEBs and higher boiling compounds, is sent via line 146 to an ethylbenzene distillation column 148. The typical amount of benzene remaining in the stream in line 146 is about 1 ppm to about 5000 ppm, about 500 ppm is preferred.

The ethylbenzene distillation column 148 separates ethylbenzene, i.e. final product, from polyethylbenzenes. The diethylbenzene concentration in line 150 is between about 1 ppm to about 50 ppm, preferably about 5 ppm. An overhead ethylbenzene vapor stream exits the ethylbenzene distillation column 148 via line 150, is liquefied in a condenser 152 and sent to an accumulator 154, and is then withdrawn via line 156 as ethylbenzene product. The condenser 152 can produce steam or can heat other process streams, and may use cooling water or air.

Line 157 carries a portion of the stream in line 156, i.e. a liquid reflux stream, to the top of the ethylbenzene distillation column 148 to maintain the distillation operation. Line 158 carries a liquid stream from the bottom of the ethylbenzene distillation column 148 to a reboiler 160. A vapor, and possibly some liquid, is returned back to the ethylbenzene distillation column 148 via line 159. This vapor drives the distillation operation in the ethylbenzene distillation column 148.

The ethylbenzene distillation column bottom stream in line 162, which comprises PEBs and higher boiling compounds, is sent to a PEB distillation column 164 for the separation of PEBs from the higher boiling compounds (e.g., heavy flux oil).

The PEB distillation column 164 separates the PEBs from the heavy flux oil, which may generally comprise tetraethylbenzene, pentaethylbenzene, diphenylmethane, 1,1-diphenylethane, 1,2-diphenylethane, sec-butylbenzene and/or other high boiling aromatics. Generally, less than about 5 wt % of the triethylbenzene is lost in the flux oil. The heavy flux oil is withdrawn as a PEB distillation column bottom stream via line 170. The flux oil can be further processed as a heat transfer fluid or used as fuel. The overhead PEB vapor is sent via line 172 to be liquefied in a condenser 174 and sent to an accumulator 176. The PEB is sent via line 178 to cooler 182 where it is cooled before being directed to the vent scrubber 108 where it is contacted with the stream from line 106. The condenser 174 can produce steam or can heat other process streams, and may use cooling water or air.

Line 179 carries a portion of the stream in line 178, i.e. a liquid reflux stream, to the top of the PEB distillation column 164 to maintain the distillation operation. Line 166 carries a liquid stream from the bottom of the PEB distillation column 164 to a reboiler 168. A vapor, and possibly some liquid, is returned back to the PEB distillation column 164 via line 167. This vapor drives the distillation operation in the PEB distillation column 164.

While the invention has been described with reference to preferred embodiments, it will be understood by those skilled in the art that various changes may be made and equivalents may be substituted for elements thereof without departing from the scope of the invention. For example, the chemical components used in practicing the invention may vary according to, at least, the olefin being used, the aromatic being alkylated and the chemical makeup of the olefin feed stock. For example, in addition to ethylene, the olefin used may include propylene or other branched or linear olefins containing 2 to at least 20 carbon atoms. The aromatic used may include, in addition to benzene, naphthalene, anthracene, phenanthrene, and derivatives thereof. Thus, ethylbenzene, cumene, and other alkylaromatics, may be produced by the processes of the invention.

Also, various components of the above-described arrangement may be replaced with other known, for example, alkylator, transalkylator, absorber and/or distillation column components. In addition, many other heat exchanger, heating and cooling configurations are possible depending on the site conditions. For example, air or water cooling and different levels of steam production may be used in the processes of the invention.

Thus, it is intended that the invention not be limited to the particular embodiments disclosed herein for carrying out the invention, but that the invention will include all embodiments falling within the scope of the appended claims.

What is claimed is:

1. A process for producing an alkylaromatic compound, comprising:
    a) contacting a dilute olefin gas feed with a liquid lean oil stream containing at least one non-alkyl aromatic compound and at least one alkylaromatic compound in an absorption zone to provide an alkylation reaction rich oil stream containing the non-alkyl aromatic compound, the alkylaromatic compound and the olefin;
    b) reacting at least some of the non-alkyl aromatic compound and at least some of the olefin in the alkylation reaction rich oil stream of step (a) under alkylation reaction conditions in an alkylation reaction zone to provide an effluent containing a portion of the non-alkyl aromatic compound and an increased amount of alkylaromatic compound;
    c) separating the effluent of step (b) into the lean oil stream which is recycled to the absorption zone of step (a) and a product portion; and,
    d) recovering an alkylaromatic product from the product portion of step (c).

2. The process of claim 1, wherein the aromatic compound is selected from the group consisting of benzene, naphthalene, anthracene and phenanthrene.

3. The process of claim 1, wherein the olefin alkylation agent is selected from the group consisting of ethylene, propylene, and branched or linear olefins containing from 4 to about 20 carbon atoms.

4. The process of claim 1, wherein the alkylaromatic compound is selected from the group consisting of alkylbenzene, polyalkylbenzene and mixtures thereof.

5. The process of claim 4, wherein the alkylbenzene is selected from the group consisting of ethylbenzene and cumene.

6. The process of claim 4, wherein the polyalkylbenzene comprising at least one benzene compound possessing two or more ethyl groups as substituents.

7. The process of claim 1, wherein the dilute olefin feed has an olefin concentration in the range of about 3 mol % to about 95 mol %.

8. The process of claim 7, wherein the dilute olefin feed has an olefin concentration in the range of about 3 mol % to about 70 mol %.

9. The process of claim 1, wherein the dilute olefin feed includes one or more inert low molecular weight impurities selected from the group consisting of hydrogen, methane, ethane, nitrogen, carbon dioxide, carbon monoxide, butane and pentane.

10. The process of claim 9, wherein the dilute olefin feed has an inert low molecular weight impurities concentration of at least about 5 mol %.

11. The process of claim 10, wherein the dilute olefin alkylation agent feed has an olefin concentration in the range of about 3 mol % to about 70 mol %.

12. The process of claim 1, wherein the absorption zone comprises an absorber selected from the group consisting of a packed column absorber, tray absorber and combined tray and packed column absorber.

13. The process of claim 12, wherein gaseous overheads from the absorber are transferred to a vent scrubber.

14. The process of claim 12, wherein the absorber operates in the gas phase.

15. The process of claim 1, wherein the alkylation reaction zone comprises an alkylator.

16. The process of claim 15, wherein the alkylator is a fixed bed reactor.

17. The process of claim 16 wherein the alkylator comprises multiple beds and multiple olefin inlets respectively positioned between the beds.

18. The process of claim 15, wherein the alkylator operates in the liquid phase.

19. The process of claim 15, wherein the alkylator contains a catalyst selected from the group consisting of zeolite BEA, zeolite MWW, zeolite Y, Mordenite catalyst, MFI catalyst and Faujasite catalyst, or combinations thereof.

20. The process of claim 1, wherein the lean oil stream in step (c) comprises about 5 wt % to about 99 wt % of the effluent of step (b).

21. The process of claim 20, wherein the lean oil stream in step (c) comprises about 75 wt % to about 95 wt % of the effluent of step (b).

22. The process of claim 1, wherein the recovery step (d) includes one or more distillation operations.

23. The process of claim 22, wherein unreacted aromatic compound is recovered in a first distillation operation and the alkylaromatic product is recovered in a second distillation operation.

24. The process of claim 23, wherein at least a portion of the unreacted aromatic compound is recycled to the lean oil stream.

25. The process of claim 1, wherein the effluent of step (b) also contains polyalkylaromatic byproduct which is recovered in a distillation operation.

26. The process of claim 25, wherein at least a portion of the recovered polyalkylaromatic byproduct is directed to a vent scrubber to provide a transalkylation reaction stream for transfer to a transalkylator.

27. The process of claim 26, wherein the transalkylation reaction stream is subjected to catalytic transalkylation reaction conditions to form a transalkylation reaction product stream having a higher aromatic to polyalkylaromatic ratio than that of the transalkylation reaction stream.

28. The process of claim 27, wherein the transalkylation reaction product stream is directed to the operations to separately recover unreacted aromatic compound and alkylaromatic compound.

29. The process of claim 1, wherein additional olefin alkylation agent is added to the alkylation reaction zone of step (b).

30. The process of claim 29, wherein the additional olefin alkylation agent is high purity ethylene.

31. The process of claim 1, wherein step (c) includes the additional step of subjecting the first portion of the alkylation product stream of step (b) to an operation to recover ethane before recycling the first portion of the alkylation product stream to the contact zone of step (a).

* * * * *